United States Patent [19]

Steffens et al.

[11] Patent Number: 6,066,482
[45] Date of Patent: May 23, 2000

[54] ACYLTRANSFERASE AND GENE ENCODING ACYLTRANSFERASE

[75] Inventors: John C. Steffens; Gurdey S. Ghangas, both of Ithaca, N.Y.

[73] Assignee: Cornell Research Foundation, Inc., Ithaca, N.Y.

[21] Appl. No.: 09/041,780

[22] Filed: Mar. 13, 1998

Related U.S. Application Data

[63] Continuation of application No. 08/665,966, Jun. 21, 1996, Pat. No. 5,756,328
[60] Provisional application No. 60/008,948, Dec. 20, 1995.
[51] Int. Cl.[7] .............................. C12P 21/06; C12N 9/00; C12N 9/10; C12N 5/10
[52] U.S. Cl. .................... 435/193; 435/183; 435/69.1; 435/72; 435/105; 435/320.1; 435/410; 435/411; 536/23.3; 930/230; 930/240
[58] Field of Search ................................ 435/183, 69.1, 435/72, 105, 320.1, 410, 411, 193; 536/23.6; 930/230, 240

[56] References Cited

PUBLICATIONS

Walker–Simmons, M., et al., Phytochemistry, vol. 19, 43–47 (1980).
Strack, D., et al., Plant Physiol. 92, 41–47 (1990).
Ghangas, G. S. and Steffens, J. C., Proc. Nat'l Acad. Sci. USA, vol. 90, pp. 9911–9915 (Nov. 1993).
Mandava, N., et al., Chem. Ind. 930–931 (1972).
Ghangas, G. S. and Steffens, J. C., Archives of Biochemistry and Biophysics, vol. 136, No. 1, 370–377 (Jan. 10, 1995).
Li, X., et al., Supplement to Plant Physiology, vol. 108, No. 2, p. 66, Abstract 288 (Jun. 12, 1995).

*Primary Examiner*—Michael P. Woodward
*Assistant Examiner*—Mary K Zeman

[57] ABSTRACT

Essentially pure acyltransferase is provided which is functional to catalyze reaction to form sugar esters. Also provided is isolated gene encoding acyltransferase. Additionally provided is method for forming palmityl esters of glucose comprising reacting 1-O-palmitoyl-β-D-glucose with itself, with glucose or with palmityl partial ester of glucose in the presence of a catalytically effective amount of acyltransferase.

4 Claims, No Drawings

ID NO: 9.

ACYLTRANSFERASE AND GENE ENCODING ACYLTRANSFERASE

CROSS-REFERENCE TO RELATED APPLICATION

This is a continuation of Ser. No. 08/665,966 filed on Jun. 21, 1996 U.S. Pat. No. 5,756,328, which claims the benefit of U.S. provisional application Ser. No. 60/008,948, filed on Dec. 20, 1995.

This invention is made in part with Government support under U.S. Department of Agriculture Grants 90-37153-5438 and 91-37300-6566. The Government has certain rights in the invention.

TECHNICAL FIELD

This invention is directed to isolation of acyltransferase for use in preparing sugar polyesters and to gene encoding acyltransferase for use in preparing sugar polyesters.

BACKGROUND OF THE INVENTION

Sugar polyesters are a diverse class of molecules including, but not limited to, glucose and sucrose esters of fatty acids and other carboxylic acids.

Partial acylation of the available hydroxyls in the sugar moiety provides feeding deterrent (pest repellent) properties (for use in agriculture), emulsification properties (for use in the food and cosmetic industries) and emollient properties (for use in the cosmetic industry). Six to eight fatty acids esterified to the eight available sucrose hydroxyls provides noncaloric fat substitute.

At present, the sugar polyesters are made through techniques of synthetic organic chemistry.

SUMMARY OF THE INVENTION

The present invention is based on isolation of an acyltransferase from a plant which catalyzes esterification reactions providing sugar esters and sugar polyesters.

In a first embodiment, the instant invention is directed to an essentially pure acyltransferase which comprises the sequence set forth in the Sequence Listing as SEQ ID NO: 8 and to an essentially pure acyltransferase which comprises the sequence set forth in the Sequence Listing as SEQ ID NO: 8 and also the sequences set forth in the Sequence Listing as SEQ ID NOS: 5 and 6.

Based on isolation of the acyltransferase, genes have been isolated which code for acyltransferase. These isolated genes are useful for preparing transgenic yeast or transgenic *E. coli* for use in manufacturing acyltransferase or for use in preparing transgenic plants transformed to contain gene coding for acyltransferase which produce sugar polyesters and which may be harvested to recover sugar polyesters.

In a second embodiment, the instant invention is directed to an isolated gene encoding an acyltransferase which comprises the sequence set forth in the Sequence Listing as SEQ ID NO: 9.

In a third embodiment, the instant invention is directed to a method of preparing palmitoyl esters of glucose which comprises reacting 1-O-palmitoyl-β-D-glucose with glucose or with palmitoyl partial ester of glucose in the presence of acyltransferase which comprises the sequence set forth in the Sequence Listing as SEQ ID NO: 8 or which comprises the sequence set forth in the Sequence Listing as SEQ ID NO. 8 and also the sequences set forth the Sequence Listing as SEQ ID NOS: 5 and 6.

The term "essentially pure" is used herein to mean meeting the criterion of purified to be free of contaminating protein, i.e., a single protein band or a plurality of protein bands representing different levels of glycosylation of the same protein or a plurality of protein bands representing a protein and subunit or subunits thereof, on a sodium dodecyl sulfate polyacrylamide gel submitted to electrophoresis under reducing, or fully denaturing, conditions and stained with Ponceau stain and/or meeting the criterion of having a specific activity of at least 35 nanokatals mg$^{-1}$.

DETAILED DESCRIPTION

Acyltransferase herein is coded for by gene of the genome of and is isolated and derived from the wild tomato species *Lycopersicon pennelli* (LA716), which is available from the Tomato Genetics Resource Center.

To purify this enzyme, leaf extract is prepared from leaves of *L. pennelli* (LA716) as described in Example I herein and the enzyme is obtained from the leaf extract and is purified therefrom in a succession of five purification steps. The first step in the purification is an ammonium sulfate precipitation step in which protein is precipitated by addition of solid ammonium sulfate, i.e., $(NH_4)_2SO_4$. Ammonium sulfate is added to the extract to 80% of saturation. This is followed by centrifugation. The supernatant is retained and dialyzed. The second step in the purification is a polyethylene glycol precipitation step. Polyethylene glycol is added to provide 0.15 g/ml. This is followed by centrifugation. After discarding of the pellet, polyethylene glycol is added again to a final concentration of 0.22 g/ml at which point protein precipitates and is collected by centrifugation. The third step in the purification involves ion exchange on DEAE (diethylaminoethoxy ion exchange moiety) sepharose. A suspension of protein from the second purification step is passed through a column containing DEAE sepharose and then elution is carried out using 0–250 millimolar KCl gradient. The active fractions are pooled and concentrated by ultrafiltration. The fourth step in the purification involves performing affinity chromatography on the concentrated active fractions from the third purification step in a column containing Concanavalin A (a protein which binds sugars, sometimes referred to as ConA). Proteins which are glycosylated bind, and since the acyltransferase being isolated is glycosylated, it binds. This fourth purification step involves washing with Tris-KOH (pH 7.5) plus 10% glycerol as loading buffer and then eluting first with the Tris buffer and 10% glycerol plus 50 mM α-methylglycoside to displace previously bound irrelevant protein and then eluting with the Tris buffer and 10% glycerol plus 100 mM α-methylglycoside to elute the enzyme of interest. The active fractions are pooled and concentrated by ultrafiltration. The fifth step in the purification involves performing HPLC on the concentrated active fractions from the fourth purification step on a chromatofocusing column under a pH gradient of 4–6. Again the active fractions are pooled and concentrated by ultrafiltration.

Assays for enzyme activity are readily carried out by measuring the disproportionation of 1-O-β-[$^{14}$C-isobutyryl] glucose to form 1-O-β-[$^{14}$C-isobutyryl]-di-O-[$^{14}$C-isobutyryl]-glucose, 1-O-β-[$^{14}$C-isobutyryl]-tri-O-[$^{14}$C-isobutyryl]-glucose, i.e., the transfer of the [$^{14}$C]isobutyryl group from 1-O-β-[$^{14}$C-isobutyryl]glucose to other 1-O-β-[$^{14}$C-isobutyryl]glucose, in the presence of sample for which enzyme activity is being determined. A preferred assay involving measuring acyl transfer is described in Example I hereinafter.

Assays for enzyme activity can also be carried out by measuring the anomeric transfer of isobutyryl from 1-O- isobutyryl-β-D-glucose to [U-$^{14}$C]-glucose. A preferred assay involving measuring anomeric transfer is as follows. The assay is performed in a total volume of 15 μL which contains 50 mM Hepes pH 7.5, 10 mM dithiothreitol, 2 mM 1-O-isobutyryl-β-D-glucose, 40 μM [U-$^{14}$C]- glucose (2×10$^5$ cpm) and 1 to 100 ng acyltransferase. The reaction is allowed to proceed at 37° C. for 30 minutes, and then loaded onto a silica gel thin-layer chromatography plate and eluted in chloroform/methanol/water (75:22:3). The thin layer plate is then dried, exposed to autoradiographic film, and upon development of the autoradiographic image, the silica gel at regions corresponding to the migration of di-, tri-, and tetra-[$^{14}$C-isobutyryl]-glucose is scraped from the plate, eluted with methanol and radioactively quantified by liquid scintillation.

The purification of the enzyme is described in detail in Example I hereinafter.

An acyltransferase enzyme purified by the above method was found to consist of two subunits of molecular mass 33 kDa and 22 kDa by sodium dodecylsulfate polyacrylamide gel electrophoresis after the enzyme was prepared under reducing conditions on comparison to migration of proteins of known molecular weight, and to have a native molecular weight of 100,000 Da on a gel permeation column, and an isoelectric point as determined by isoelectric focusing on a 5% polyacrylamide native gel with a 3.5 to 9 pH gradient, of 5.2.

Seven peptide fractions obtained from the acyltransferase by treatment with trypsin and separation of the resulting peptides by reversed-phase high pressure liquid chromatography (HPLC) were determined to have the sequences set forth in the Sequence Listing as SEQ ID NOS: 1–7. A sequence of portion of the acyltransferase consistent with the sequence of isolated gene obtained based on the seven peptide fractions is set forth in the Sequence Listing as SEQ ID NO: 8.

The acyltransferase is functional to catalyze anomeric transfer of the acyl substituent from 1-O-acyl-β-D-glucose to glucose, 2-deoxyglucose, 3-O-methyl glucose or partially acylated glucose and to catalyze disproportionation between two molecules of 1-O-acyl-β-D-glucose resulting in formation of diacylglucose and glucose. The acyl substituent including that in the partially acylated glucose can contain, for example, from 1 to 18 carbon atoms and can be branched or straight chain and saturated or unsaturated and can be, for example, isobutanoyl or lauroyl or palmitoyl.

Reaction with 1-O-palmitoyl-β-D-glucose is considered unexpected since this reaction has not been found in nature.

The reaction involving anomeric transfer of acyl from 1-O-acyl-β-D-glucose to glucose, 2-deoxyglucose, 3-O-methyl glucose or partially acylated glucose is readily carried out using a stoichiometric amount of 1-O-acyl-β-D-glucose in buffer or aqueous media at pH ranging from 6.5 to 7.5 at 20 to 40° C. for 10 to 60 minutes in the presence of a catalytically effective amount, e.g., 0.01 to 1 μg of purified acyltransferase per mmol 1-O-acyl-β-D-glucose.

The reaction involving disproportionation is readily carried out in buffer or aqueous media at pH ranging from 6.5 to 7.5 at 20 to 40° C. for 10 to 60 minutes in the presence of a catalytically effective amount, e.g., 0.01 to 1 μg of purified acyltransferase per mmol 1-O-acyl-β-D-glucose.

The 1-O-acyl-β-D-glucose starting material can be prepared, for example, by condensing α-acetobromoglucose and isobutyric acid followed by deacetylation with sunflower esterase. Alternatively, the 1-O-acyl-β-D-glucose can be prepared by reacting acyl chloride with tetrabenzylglucose in dry benzene at 62° C. and deprotecting according to the procedure of Pfeffer, P. E., et al., J. Org. Chem 41, 2925–2927 (1976).

We turn now to the isolation of gene coding for an acyltransferase which catalyzes esterification reactions providing sugar esters and sugar polyesters. Detached trichomes are prepared from L. pennelli leaves by the dry ice abrasion method as described in Yerger, E. H., et al., Plant Physiol 99, 1–7 (1992). The trichomes are suspended in buffer, total RNA extracted and mRNA purified according to the method described in Hunt, M. D., et al, Plant Molec. Biol. 21, 59–68 (1993). The acyltransferase gene is cloned following procedures described by Frohman, M. A., et al., Proc. Natl. Acad. Sci. USA 85:8998–9002 (1988), and Loh, E. Y., et al., Science 243:217–220 (1980). Gene fragment consisting of an internal portion of the gene coding for the acyltransferase is obtained as follows from the total purified mRNA. Total purified mRNA is reversed transcribed into cDNA using oligo (dT)$_{15}$ and reverse transcriptase. Aliquot of resulting mixture is then used for polymerase chain reaction in a reaction mixture containing a primer mix corresponding to the least degenerate two of the aforementioned seven peptide fragments and Taq polymerase. The polymerase chain reaction products are analyzed by agarose gel electrophoresis and the major amplification product is excised from the gel, eluted and purified and ligated into PCRII vector for sequencing and the sequence is determined. A gene fragment including the 5' end of the gene is then obtained as follows from the total purified mRNA. Aliquot of mixture resulting from reverse transcription of total purified mRNA is primed with a gene-specific primer (based on a portion of the sequence determined for the 5' end of middle fragment). The resulting cDNA is dc-tailed at the 5' end and the 5' end is amplified by polymerase chain reaction using a nested primer having sequence based on another portion of the sequence determined for the 5' end of middle fragment and an anchor primer and the major amplification product is excised and recovered as described above and cloned into pAMP1 for sequencing and the sequence of the 5' end is determined. Next a gene fragment including the 3' end of the gene is obtained as follows from the total purified mRNA. Aliquot of resulting mixture from reverse transcription of total purified mRNA is amplified using polymerase chain reaction using a gene specific primer (based on a portion of the sequence determined for the 3' end of middle fragment) and a second round of polymerase chain reaction using a nested primer is used to provide enrichment of 3' end cDNA fragment. The polymerase chain reaction product representing the 3' end of the cDNA is cloned into pAMP1 vector for sequencing and is sequenced. Having cloned and sequenced the 5' and 3' ends of the cDNA, primers are synthesized corresponding to these ends and also incorporating BamHI and EcoRI restriction sites and these are used to amplify the entire gene sequence following the procedures described above. The gene is then cloned into the E. coli vector pBluescript which has been prepared with BamHI and EcoRI and transformed into XL1-blue cells for sequencing and sequencing provides the sequence of the entire gene. A detailed description of the isolation and identification of gene coding for acyltransferase from L. pennelli (LA716) is set forth in Example II hereinafter. Sequencing of the gene provided the sequence set forth in the Sequence Listing as SEQ ID NO: 9. The amino acid sequence corresponding to base pairs 1–54 of the nucleic acid sequence of SEQ ID NO: 9 constitutes a signal peptide. Thus, the peptide of SEQ ID NO: 1 is the fragment at the N-terminus of the enzyme. The nucleic acid sequence of SEQ ID NO: 9 indicates a discrepancy in portion corresponding to the peptide fragment of SEQ ID NO: 4 in that it indicates that the amino acid for position number 3 of the sequence of SEQ ID NO: 4 is Phe instead of Ile. Furthermore, the nucleic acid sequence of SEQ ID NO: 9 indicates a discrepancy in portion corresponding to the peptide fragment of SEQ ID NO: 7 in that it indicates that the amino acid for the position number 14 in SEQ ID NO: 7 is Cys instead of Leu. The nucleic acid sequence of SEQ ID NO: 9 after the signal peptide corresponding to base pairs 1–54 is accounted for, indicates that the acyltransferase coded for by the remainder of the base pairs should contain 446 amino acids and have a molecular mass of about 49 kDa and have the sequence set forth in the Sequence Listing as SEQ ID NO.: 10. This indicates that the acyltransferase herein is encoded by a small gene family and that the gene that was isolated was slightly different from the gene encoding the acyltransferase that was isolated.

The difference between the molecular mass determined by sodium dodecylsulfate polyacrylamide gel electrophoresis (subunit molecular masses of 33 kDa and 22 kDa for a total of 55 kDa) and that predicted for the mature protein from the sequence of the isolated gene (49 kDa) is not an unusual observation and is not of concern. The protein is glycosylated and this may result in electrophoretic behavior inconsistent with the mass of the polypeptide. Also a skewed amino acid composition of a small fragment ($\leq$20 kDa) may result in anomalous migration on sodium dodecyl sulfate polyacrylamide gel electrophoresis.

The isolated gene is transferred into yeast by inserting the entire acyltransferase cDNA sequence into the *Saccharomyces cerevisiae* expression vector pYES2, to generate a plasmid pYAGT2 and transforming pYAGT2 into *S. cerevisiae*; expression is achieved by induction with galactose. A suitable procedure is described in more detail in Example III.

The isolated gene is transferred into *E. coli* (e.g., *E. coli* XL-Blue supplied by Stratagene) by cloning into pBluescript and transforming the resulting plasmid into *E. coli* via electroporation; expression is achieved by induction of the lac promoter using X-Gal (supplied by Stratagene) according to supplier's instructions.

The isolated gene is used to transform a plant, e.g., a tobacco plant, by the procedures described in Fraley, R. F., et al., CRC Critical Reviews in Plant Sciences 4: 1–86 (1986).

The embodiments of the invention are illustrated in the following working examples:

EXAMPLE I
Isolation and Characterization of Acyltransferase from *L. pennelli* (LA716)

*L. pennelli* (LA716) seeds were obtained from Tomato Genetics Resource Center, Department of Vegetable Crops, University of California, Davis, Calif. 95616–8746, and were grown in the greenhouse. The "LA" designation is the Lycopersicon accession number. The original seed was collected on Feb. 16, 1958 by Donovan Correll at the Pacific face of the southern Peruvian Andes (latitude, 16 degrees S, by longitude 73–74 degrees W) and was deposited and accessioned in 1959. The plant of LA716 is described at pages 39–41 of Correll, Donovan Stewart, "The Potato and Its Wild Relative", Texas Research Foundation, Renner, Tex., 1962.

The following procedure was used to obtain leaf extracts: 200 g of frozen leaves and stem tissue was homogenized in 500 ml of 50 mm Hepes·NaOH, pH 7.0/250 mM sucrose (functions to stabilize protein)/10 mM dithiothreitol(inhibits oxidative browning of extract)/1% (w/v) acid-washed polyvinyl pyrrolidone (binds phenolics)/0.1% (w/v) diethyldithiocarbamate (inhibits polyphenol oxidases). The homogenate was centrifuged at 15,000×g for 20 minutes to remove debris. The supernatant was adjusted to 80% saturation with solid $(NH_4)_2SO_4$ and, after 30 minutes on ice, was centrifuged at 20,000×g for 30 min. The pellet was suspended in 10 ml of 50 mM Hepes·NaOH, pH 7.0/1 mM dithiothreitol/0.5 mM phenylmethylsulfonylfluoride (inhibits protease activity)/10% (vol/vol) glycerol (functions to stabilize protein) and dialyzed against the same buffer. The specific activity of acyltransferase at this stage was $7.2 \times 10^{-3}$ nkatal/mg.

The dialyzed extract was then precipitated using 0.15 to 0.22 g/ml solid polyethylene glycol (mol. wt. 3,350). The pellet resulting after centrifugation at 20,000×g for 30 min. was resuspended in 50 mM Hepes-NaOH, pH 7.0, 1 mM dithiothreitol, 0.5 mM phenylmethylsulfonylfluoride, 10% (v/v) glycerol. This resulted in a 5-fold purification of the acyltransferase activity, i.e., to a specific activity of $3.7 \times 10^{-2}$ nkatal/mg. This preparation was loaded on a DEAE-Sepharose column equilibrated in the same buffer, washed with ten column volumes of buffer, and eluted with a 0 to 250 mM KCl gradient. Acyltransferase activity of each fraction was monitored by enzymatic activity, and the most active fractions, which eluted around 150 mM KCl, were pooled and concentrated by ultrafiltration, yielding a 23-fold purification, i.e., to a specific activity of 0.17 nkatal/mg. The sample was then loaded on a ConA column, and washed with ten volumes of loading buffer. The column was then washed with a 50 mL portion of loading buffer brought to 50 mM α-methyl glucoside. The acyltransferase activity was then eluted with 100 mM α-methyl glucoside. The sample was then dialyzed against 50 mM Hepes-NaOH, pH 7.0 and 10% (v/v) glycerol and concentrated by ultrafiltration, resulting in a 1,274-fold purification of acyltransferase activity, i.e., to a specific activity of 9.4 nkatal/mg. This preparation was then loaded on a Mono P high pressure liquid chromatography chromatofocusing column, from which it eluted at a pH of 4.8, resulting in a 5000-fold overall purification, i.e., to a specific activity of 36 nkatal/mg.

The acyltransferase enzyme product was determined to consist of two subunits of molecular mass 33 kDa and 22 kDa by sodium dodecyl sulfate polyacrylamide gel electrophoresis after the enzyme was prepared under reducing conditions on comparison to migration of proteins of known molecular weight. The standard proteins used to obtain this data were obtained from Sigma Chemical Co. and have molecular weights ranging from 66 to 14.3. These standard proteins and their molecular weights are bovine serum albumin (66 kDa), ovalbumin (45 kDa), glyceraldehyde-3-phosphate dehydrogenase (36 kDa), carbonic anhydrase (29 kDa), trypsinogen (24 kDa), trypsin inhibitor (20 kDa), and α-lactalbumin (14.3 kDa).

Molecular weight of the native enzyme was determined using Sephadex G100 column eluted with 50 mM Hepes-NaOH, pH 7.0 and 10% (v/v) glycerol. Molecular weight markers consisted of aprotinin (6.5 kDa), cytochrome c (12.4 kDa), carbonic anhydrase (29.0 kDa), serum albumin (66.0 kDa), and alcohol dehydrogenase (150 kDa). Under these conditions the acyltransferase exhibited a relative molecular mass of 100 kDa.

The isoelectric point of the enzyme was determined by electrofocusing on a 5% polyacrylamide native gel with a 3.5 to 9 pH gradient. When electrofocusing was complete, the gel was sliced horizontally into 2 mM bands each of which was suspended in H$_2$O. The pH of these suspensions was measured directly and an aliquot of each tested for acyltransferase activity. The enzyme was shown to possess a pI of 5.2 under these conditions.

The 5000-fold purified acyltransferase was loaded on SDS-PAGE and electroblotted onto a poly (vinylidene difluoride) membrane following the art described by Matsudaira (Methods in Enzymology 182: 602–613 (1990). The membrane was stained with Ponceau stain and the band containing the enzyme excised and destained in methanol, and resuspended in H$_2$O. The destained membrane was treated with trypsin and the resulting proteolytic products separated by high pressure liquid chromatography using a gradient from 0.1% aqueous trifluoroacetic acid to 100% acetonitrile, 0.1% trifluoroacetic acid. Seven of the resulting polypeptides were sufficiently homogeneous to sequence using automated Edman degradation procedures, and were determined respectively to have the sequences of SEQ ID NOS: 1–7.

The assays for enzyme activity in the purification steps were carried out by measuring the disproportionation of 1-O-β-[$^{14}$C-isobutyryl]glucose to di-, tri-, and tetra-isobutyryl glucose, i.e., the transfer of the [$^{14}$C]isobutyryl group from 1-O-β-[$^{14}$C-isobutyryl]glucose to other 1-O-β-[$^{14}$C-isobutyryl]glucose, in the presence of sample for which enzyme activity was being determined.

Disproportionation activity was measured by intermolecular transfer of the [$^{14}$C-isobutyryl] moiety from donor 1-O-β-[$^{14}$C-isobutyryl]-β-D-glucoses to recipient 1-O-β-[$^{14}$C-isobutyryl]-β-D-glucoses, resulting in formation of higher-order glucose esters of isobutyrate. Reactions were performed in a total volume of 15 μL which contained 50 mM Hepes, pH 7.5, 10 mM dithiothreitol, 1 mM 1-O-[$^{14}$C-isobutyryl]-β-D-glucose (10$^5$ cpm), and 1 to 100 ng acyltransferase. The reaction was allowed to proceed at 37° C. for 30 min., and then loaded onto a silica gel thin-layer chromatography plate and eluted in chloroform/methanol/water (75:22:3). The thin-layer plate was then dried, exposed to autoradiographic film, and upon development of the autoradiographic image, the silica gel at regions corresponding to the point of migration of di-, tri-, and tetra-[$^{14}$C-isobutyryl]-glucose was scraped from the plate, eluted with methanol, and radioactivity quantified by liquid scintillation.

The purified enzyme was tested for activity against the carboxypeptidase substrates carbobenzoxy-phe-ala, carbobenzoxy phe- leu, carbobenzoxy-gly-phe and carbobenzoxy-pro-phe. No activity was detected against any of these substrates.

EXAMPLE II
Isolation of Gene Coding for Acyltransferase from *L. pennelli* (LA716)

Detached trichomes were obtained from leaves of *L. pennelli* (LA716) by dry ice abrasion as described in Yerger, E. H., et al., Plant Physiol 99, 1–7 (1992) except that pulverized dry ice was first sieved through a fiberglass screen (1.4 mm$^2$ mesh). The trichomes were suspended in freshly prepared Tris·HCl, pH 7.0 (buffer)/1 mM MgCl$_2$ (stabilizer of protein structure and enzymatic activity)/0.1% diethyldithiocarbamate (acts as copper chelator to inhibit polyphenol oxidase)/0.1% dithiothreitol (acts as copper chelator to inhibit polyphenol oxidase and as scavenger of quinones, the reaction product of polyphenol oxidase)/2% polyvinylpolypyrrolidone (inhibitor of polyphenol oxidase; acts as scavenger of phenolics, the substrates for polyphenol oxidase).

Total RNA was extracted from the trichomic suspension and mRNA was purified according to the method described in Hunt, M. D., et al., Plant Molec. Biol. 21, 59–68 (1993).

Acyltransferase gene was cloned following procedures described by Frohman, M. A., et al., Proc. Natl. Acad. Sci. USA 85:8998–9002 (1988), and Loh, E. Y., et al., Science 243:217–220 (1980).

Sequence of an internal fragment of the gene coding for acyltransferase gene was determined as follows:

The purified mRNA was reversed transcribed into cDNA using olig (dT)$_{15}$ and reverse transcriptase (Superscript II RNase H-, Gibco-BRL, used with 0.1 μg mRNA in 10 μL reaction according to manufacturer's instructions).

One μL resulting mixture was then used for polymerase chain reaction in a 100 μL reaction mixture containing 10 mM Tris-HCl 8.3, 50 mM KCl, 1.5 mM MgCl$_2$, 0.1% (w/v) gelatin, 200 μM dNTPs, 3.2 μM of 20 base primer PT 50 (having the sequence set forth in the Sequence Listing as SEQ ID NO: 11), 1.6 μM primer RE24 (having the Sequence Listing as SEQ ID NO: 12, and 2.5 Units Taq polymerase. In the sequence of SEQ ID NO: 12, N stands for inosine. The primers PT50 and RE24 correspond to the least degenerate two of the seven polypeptides referred to and described in terms of sequences in Example I. Polymerase chain reaction was carried out in 34 cycles of denaturing (92° C., 1 min.), annealing (50° C., 40 sec.), and polymerization (72° C., 1 min.) and one cycle of 72° C., 10 min. The polymerase chain reaction products were analyzed by agarose gel electrophoresis and the major amplification product was excised from the gel, eluted and purified using GeneCleanII nucleic acid clean up kit (available from Bio 101), following the manufacturer's instructions, and ligated into PCRII vector (supplied by Invitrogen) following the ATR cloning method (provided by Invitrogen). DNA sequencing was carried out to verify the amplified fragment as a component of the acyltransferase gene and to identify the sequences corresponding to the tryptic peptides (corresponding to the primers used) obtained from the purified enzyme and to provide sequencing information for primers to obtain the 5' and 3' ends of the acyltransferase gene as described below.

Gene fragment including the 5' end of the gene was then obtained as follows: Aliquot of mixture resulting from the reverse transcription of total purified mRNA was primed with a 20 base pair gene-specific primer having the sequence set forth in the Sequence Listing SEQ ID NO: 13 (based on a portion of the sequence determined as described above for 5' end of middle fragment). The resulting cDNA was dC-tailed at the 5' end and the 5' end was amplified by polymerase chain reaction using a 20 base pair nested primer having the sequence set forth in the Sequence Listing as SEQ ID NO: 14 (based on another portion of the sequence determined as described above for the 5' end of the middle fragment) and an anchor primer having the sequence set forth in the Sequence Listing as SEQ ID NO: 15 (Gibco-BRL catalog #18388–017). In the sequence of SEQ ID NO: 15, N is inosine. The major amplification product is excised and recovered as described above and cloned into pAMP1 (Gibco-BRL), following the manufacturer's instructions, and sequenced.

Next gene fragment including the 3' end of the gene was obtained as follows: cDNA was synthesized from purified mRNA using reverse transcription primed with Oligo (dT) primer attached to an adapter primer. The 3' end of the cDNA was amplified using Gibco-BRL 3' RACE (rapid amplification of cDNA ends) kit. In a first round of amplification, a 20 base pair primer (based on a portion of the sequence determined as described above for the 3' end of the middle fragment) having the sequence set forth in the Sequence Listing as SEQ ID NO: 16, was used. A second round of polymerase chain reaction was then carried out using a 20 base pair nested primer (based on another portion of the sequence determinated as described above for the 3' end of the middle fragment) having the sequence set forth in the Sequence Listing as SEQ ID NO: 17, to enrich the 3' end cDNA fragment. The polymerase chain reaction product was cloned into pAMP1 (Gibco-BRL) following the manufacturer's instructions, and sequenced.

Having cloned and sequenced the 5' and 3' ends of the cDNA, primers were synthesized corresponding to these ends and also incorporating BamHI and EcoRI restriction sites and these were used to amplify the entire acyltransferase gene sequence from the cDNA obtained from purified mRNA. The primers used respectively had the sequence set forth in the Sequence Listing as SEQ ID NO: 18 (includes a BamHI restriction site as the first nine bases of the sequence) and the sequence set forth in the Sequence Listing as SEQ ID NO: 19 (includes an EcoRI restriction site as the first seven bases of the sequence). The amplified entire gene was cloned into the E. coli vector pBluescript (supplied by Stratagene) which was prepared with BamHI and EcoRI and transformed into XL1-Blue E. coli cells (from Stratagene) according to the supplier's instructions, for sequencing.

The gene was sequenced by automatic DNA sequencing and was determined to have the sequence set forth in the Sequence Listing as SEQ ID NO: 9.

EXAMPLE III

Transformation of Gene Coding for Acyltransferase into S. cerevisiae and Induction of Expression of Acyltransferase A. Construction of Expression Clone pYAGT2 by Inserting Entire Acyltransferase cDNA Seauence into the Saccharomyces cerevisiae Expression Vector pYES2, to Generate Plasmid pYAGT2

Oligonucleotide primers corresponding to the acyltransferase 5' and 3' ends and incorporating BamHI and EcoRI restriction sites were used to amplify the gene (isolated in Example II) directly from the cDNA by polymerase chain reaction. The primers respectively have the sequences set forth in the Sequence Listing as SEQ ID NO: 18 and as SEQ ID NO: 19. After purification and treatment with BamHI and EcoRI, the gene was ligated, using T4 DNA ligase, to the Saccharomyces cerevisiae expression vector pYES2 (Invitrogen), which was prepared by the same restriction enzymes. The resulting plasmid was designated pYAGT2. To verify that correct gene was ligated, the ligation reaction was transformed into XL-1Blue E. coli cells, and the correctly ligated products from transformants were verified by DNA sequencing. The plasmid pYAGT2 was deposited with the American Type Culture Collection, 12301 Parklawn Drive, Rockville, Md. 20852 on Jun. 15, 1996 under the terms of the Budapest Treaty and has been assigned accession number ATCC 97613.

B. Transforming pYAGT2 into S. cerevisiae

S. cerevisiae strain KT1115 (MATa leu2-3 leu2-112 ura-52) is used as the recipient cell type for pYES2 transformation following the procedures described by Gietz, D., et al., Nucleic Acids Research 20:1425 (1992). Uracil dropout medium (Short Protocols in Molecular Biology, A Compendium of Methods from Current Protocols in Molecular Biology, Ausubel, F. M., et al., editors, 2nd Edition, Green Publishing Associates and John Wiley and Sons, New York, 1992) was used as selective medium.

C. Induction of Expression of Protein Encoded by the Recombinant Plasmid

Baffled flasks were used to grow yeast cultures for the expression of the L. pennelli acyltransferase. Transformed yeast cells were inoculated in uracil dropout medium (with 5% (w/v) raffinose instead of 2% (w/v) glucose), until $OD_{600}$ reached 0.4 to 0.5. Galactose was then added to a final concentration of 2% (w/v) to induce expression of the protein. 10 mL samples were collected at 4, 8, 24 and 48 hours after the addition of galactose.

D. Determination of Expressed Protein as Being Acyltransferase

Induced cells were centrifuged, washed with cold $H_2O$ and then with cold FT buffer, i.e., freeze and thaw buffer: 100 mM Hepes, pH 7.5, 20% (v/v) glycerol, 0.1% (v/v) Triton X-100). The pelleted cells were resuspended in an equal volume of cold FT buffer and frozen at −80° C. overnight or longer. For assay for activity, the permeabilized cells were thawed quickly at 30° C. and an aliquot removed as described by Miozzari (Miozzari, G. F., et al., Analytical Biochemistry 90:220–233 (1978)). When 10 mL of cells were removed for assay under standard conditions for measurement of acyltransferase activity using 1-O-[$^{14}$C-isobutyryl]-β-glucose as described above, S. cerevisiae cells transformed with only the pYES2 vector do not possess detectable acyltransferase activity giving rise to higher-order glucose esters at any time-point after induction with galactose. However, S. cerevisiae cells harboring the pYAGT2 plasmid containing the acyltransferase gene exhibited the ability to form higher-order esters at 4, 8 and 24 hours after induction with galactose showing acyltransferase activity was expressed. Highest activity was found 24 hours after induction, and activity at 48 hours was slightly lower than at 24 hours.

EXAMPLE IV

Preparation of Monopalmitoyl Glucose from 1-O-Palmitoyl-β-D-glucose and Glucose

Tetrabenzylglucose (1.8 g, 3.3 mmol), Pfanstiehl Chemical Co., was reacted with palmitoyl chloride (Sigma Chemical Co.) in dry benzene at 62° C. and deprotected by the procedure of Pfeffer, P. E., et al., J. Org. Chem. 41, 2925–2927 (1976), to produce 1-O-palmitoyl-β-D-glucose.

A reaction mix was made up containing 2 mM 1-O-palmitoyl-β-D-glucose, 40 μM [U-$^{14}$C] glucose (2×10$^5$ cpm) and 1 mg/ml of acyltransferase protein (specific activity of 4×10$^{-2}$ nanokatals mg$^{-1}$) in 15 μl of a mixture of 50 mm Hepes-NaOH, pH 7.0 (buffer), 10 mM $MgCl_2$ (stabilizer of protein structure and enzymymatic activity), and 10 mM dithiothreitol (inhibitor of polyphenol oxidase; acts as copper chelator and as scavenger of quinones, the reaction product of polyphenol oxidase; also promotes higher order esterification presumably by maintaining essential Cys residues of the acyltransferase in reduced form) and incubation was carried out at 37° C. Reaction progress was monitored by TLC as described in Ghangas, G. S. et al., Proc. Natl. Acad. Sci. USA 90, 9911–9915 (1993). The % cpm in monoacyl-[$^{14}$C] glucose was 2.3 after 1 hour, 4.4 after 2 hours and 4.7 after 3 hours.

When 1-O-isobutyryl-β-D-glucose was substituted for the 1-O-palmitoyl-β-D-glucose, the % cpm in monoacyl-[$^{14}$C] glucose was 3.08 after 1 hour, 5.80 after 2 hours, and 6.20 after 3 hours.

EXAMPLE V

Preparation of Dipalmitoyl Glucose from 1-O-palmitoyl-β-D-glucose

1-O-Palmitoyl-β-D-glucose (0.1 mM) and 80 μM [U-$^{14}$C] glucose (2×10$^7$ cpm) were incubated with 1 mg acyltransferase (specific activity of about 0.037 nanokatals mg$^{-1}$) from L. pennelli in 0.5 ml 50 mM sodium Pi, pH 6.5, for 2 hours at 42° C. The reaction was stopped by addition of 1 ml of chilled ethanol, and after centrifugation, the supernatant was recovered, concentrated, and applied to a preparative TLC plate to isolate the 1-O-palmitoyl-β-D-[$^{14}$C-glucose] band.

Reaction mix was made up containing 3×10⁴ cpm 1-O-palmitoyl-β-D-[¹⁴C-glucose], 50 mM Hepes-NaOH, pH 7.0, 10 mM dithiothreitol (inhibits oxidation browning), 10 mM MgCl₂ (protein structure stabilizer) and acyltransferase (3.6 mg/mL protein; specific activity of about 0.037 nanokatal mg⁻¹) from *L. pennelli* in 15 μl were incubated at 37° C. The products were separated and monitored by TLC as described in Ghangas, G. S., et al., Proc. Natl. Acad. Sci. USA 90, 9911–9915 (1993). The percent of total cpm in [¹⁴C] glucose by-product was 40% indicating that the disproportion reaction had occurred to provide dipalmitoyl glucose.

When 1-O-isobutyryl-β-D-glucose was substituted for the 1-O-palmitoyl-β-D-glucose, the percent of total cpm in [¹⁴C] glucose by-product was 44.8% indicating that the disproportion reaction had occurred to provide diisobutyryl glucose.

EXAMPLE VI

Preparation of Tripalmitoyl Glucose from 1-O-Palmitoyl-β-D-glucose

A 15 μL reaction containing 1-O-palmitoyl-β-D-glucose (1 mM), [U-¹⁴C]-glucose (2×10⁵ cpm), and 2.5 mg *L. pennelli* LA716 crude leaf extract protein/ml in 100 mM sodium phosphate pH 6.5 was incubated for 28 hr at 37° C. The products were separated and monitored by TLC as described in Ghangas G S and Steffens J C, Proc. Natl. Acad. Sci. USA 90:9911–9915 (November, 1993). The percent of total cpm converted to tripalmitoylglucose was equivalent to 8 pmol. Formation of mono- and dipalmitoylglucose in the same reaction was 2660 and 459 pmol, respectively. Under the same conditions 1-O-isobutyryl-β-D-glucose yielded 3410, 34 and 14 pmol mono-, di- and triisobutryrylglucose, respectively.

Variations in the invention will be obvious to those skilled in the art. Therefore, the invention is defined by the claims.

What is claimed is:

1. A purified acyltransferase which catalyzes transfer of $C_1$–$C_{18}$ straight or branched chain, saturated or unsaturated acyl substituents to produce sugar esters and sugar polyesters with $C_1$–$C_{18}$ straight or branched chain, saturated or unsaturated acyl substituents comprising amino acid sequences as set forth in the Sequence Listing as SEQ ID NOS. 1–7 except that the amino acid at position number 3 for SEQ ID NO. 4 is Phe or Ile and except that the amino acid at the position number 14 for SEQ ID NO. 7 is Cys or Leu.

2. A purified acyltransferase which catalyzes transfer of $C_1$–$C_{18}$ straight or branched chain, saturated or unsaturated acyl substituents to produce sugar esters and sugar polyesters with $C_1$–$C_{18}$ straight or branched chain, saturated or unsaturated acyl substituents, comprising an amino acid sequence with no more than one amino acid different from the sequence of SEQ ID NO:4.

3. A purified acyltransferase which catalyzes transfer of $C_1$–$C_{18}$ straight or branched chain, saturated or unsaturated acyl substituents to produce sugar esters and sugar polyesters with $C_1$–$C_{18}$ straight or branched chain, saturated or unsaturated acyl substituents, comprising an amino acid sequence with no more than one amino acid different from the sequence of SEQ ID NO:7.

4. An isolated DNA molecule encoding acyltransferase which catalyzes transfer of $C_1$–$C_{18}$ straight or branched chain, saturated or unsaturated acyl substituents to produce sugar esters and sugar polyesters with $C_1$–$C_{18}$ straight or branched chain, saturated or unsaturated acyl substituents.

* * * * *

```
                        SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (xi) SEQUENCE DESCRIPTION: SEQ ID NO:1:

Glu His Phe Ile Val Glu Thr Leu Pro Gly Phe His
1               5                   10

(2) INFORMATION FOR SEQ ID NO:2:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:2:

Leu Glu Leu Asn Ser Tyr Ser Trp
1               5

(2) INFORMATION FOR SEQ ID NO:3:

(i) SEQUENCE CHARACTERISTICS:
          (A) LENGTH: 11 amino acids
          (B) TYPE: amino acid
          (D) TOPOLOGY: linear (ii) MOLECULE TYPE: peptide (xi) SEQUENCE DESCRIPTION: SEQ ID NO:3:

Ile Tyr Asp Gly Ile Glu Val Gly Asp Arg Pro
1               5                   10
```

```
(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:4:

Gly Tyr Ile Gln Gly Asn Ala Leu Thr Asp Arg
1               5                  10

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:5:

Ser Ile Asp Phe Asn Gly Arg
1               5

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:6:

Tyr Ala Asn His Met Gly Leu Ile Ser Asp Lys
1               5                  10

(2) INFORMATION FOR SEQ ID NO:7:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:7:

Asn Gly Asn Tyr Ile Asp Val Asp Pro Asn Asn Ile Leu Leu Leu Asn
1               5                  10                  15

Asp (2) INFORMATION FOR SEQ ID NO:8:

(i) SEQUENCE CHARACTERISTICS:
        (A) LENGTH: 179 amino acids
        (B) TYPE: amino acid
        (D) TOPOLOGY: linear (ii) MOLECULE TYPE: peptide (xi) SEQUENCE DESCRIPTION: SEQ ID NO:8:

Glu His Phe Ile Val Glu Thr Leu Pro Gly Phe His Gly Lys Leu Pro
1               5                  10                  15

Phe Leu Thr Glu Thr Gly Thr Ile Ser Val Gly Glu Glu Glu Lys Val
            20                  25                  30
```

```
Gln Leu Phe Tyr Phe Phe Val Gln Ser Glu Arg Asp Pro Arg Asn Asp
         35                  40                  45

Pro Leu Met Ile Trp Leu Thr Gly Gly Pro Gly Cys Ser Gly Leu Ser
 50                  55                  60

Ser Leu Val Tyr Glu Ile Gly Pro Leu Thr Phe Asp Tyr Ala Asn Ser
 65                  70                  75                  80

Ser Gly Asn Phe Pro Lys Leu Glu Leu Asn Ser Tyr Ser Tyr Thr Lys
                 85                  90                  95

Val Ala Asn Ile Ile Phe Ile Asp Gln Pro Ala Gly Thr Gly Tyr Ser
                100                 105                 110

Tyr Ala Asn Thr Ser Glu Ala Tyr Asn Cys Asn Asp Thr Leu Ser Val
            115                 120                 125

Thr Leu Thr Tyr Asp Phe Leu Arg Lys Trp Leu Met Asp His Pro Glu
130                 135                 140

Tyr Leu Asn Asn Pro Leu Tyr Val Gly Gly Asp Ser Tyr Ser Gly Ile
145                 150                 155                 160

Phe Val Ala Leu Leu Thr Arg Lys Ile Tyr Asp Gly Ile Glu Val Gly
                165                 170                 175

Asp Arg Pro
```

(2) INFORMATION FOR SEQ ID NO:9:

(i) SEQUENCE CHARACTERISTICS:
      (A) LENGTH: 1604 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 55..1392

(xi) SEQUENCE DESCRIPTION: SEQ ID NO:9:

```
ATGGCGCGGG TCACACTGTT TCTATTGCTG CTACTTGTAT ACGGTGTAGT CTCC GAG        57
                                                           Glu
                                                             1

CAC TTC ATT GTT GAA ACT CTT CCT GGG TTT CAT GGA AAA CTT CCA TTT       105
His Phe Ile Val Glu Thr Leu Pro Gly Phe His Gly Lys Leu Pro Phe
          5                  10                  15

ACA CTC GAA ACT GGT TAT ATT AGT GTT GGA GAA GAG GAA AAA GTG CAG       153
Thr Leu Glu Thr Gly Tyr Ile Ser Val Gly Glu Glu Glu Lys Val Gln
         20                  25                  30

CTA TTT TAT TTC TTT GTA CAA TCT GAG AGA GAC CCA CGA AAT GAT CCT       201
Leu Phe Tyr Phe Phe Val Gln Ser Glu Arg Asp Pro Arg Asn Asp Pro
     35                  40                  45

CTC ATG ATT TGG CTC ACC GGA GGT CCT GGT TGT TCT GGT CTG TCT TCC       249
Leu Met Ile Trp Leu Thr Gly Gly Pro Gly Cys Ser Gly Leu Ser Ser
 50                  55                  60                  65

TTA GTA TAT GAA ATT GGC CCT TTA ACC TTT GAT TAT GCA AAT TCT AGT       297
Leu Val Tyr Glu Ile Gly Pro Leu Thr Phe Asp Tyr Ala Asn Ser Ser
                 70                  75                  80

GGA AAT TTC CCG AAA CTG GAG TTG AAC TCA TAT TCT TGG ACC AAG GTG       345
Gly Asn Phe Pro Lys Leu Glu Leu Asn Ser Tyr Ser Trp Thr Lys Val
             85                  90                  95

GCA AAC ATA ATA TTT ATA GAT CAA CCT GCT GGC ACA GGC TAC TCA TAT       393
Ala Asn Ile Ile Phe Ile Asp Gln Pro Ala Gly Thr Gly Tyr Ser Tyr
        100                 105                 110

GCA AAC ACT TCA GAA GCT TAC AAC TGC AAT GAT ACC CTC TCT GTA ACT       441
```

-continued

```
              Ala Asn Thr Ser Glu Ala Tyr Asn Cys Asn Asp Thr Leu Ser Val Thr
                  115                 120                 125

CTA ACT TAT GAC TTC CTT AGA AAG TGG CTT ATG GAT CAT CCC GAG TAT          489
Leu Thr Tyr Asp Phe Leu Arg Lys Trp Leu Met Asp His Pro Glu Tyr
130                 135                 140                 145

CTC AAC AAT CCA CTA TAT GTT GGT GGT GAT TCC TAC TCA GGC ATT TTT          537
Leu Asn Asn Pro Leu Tyr Val Gly Gly Asp Ser Tyr Ser Gly Ile Phe
                150                 155                 160

GTT GCA CTG CTT ACT CGC AAA ATA TAC GAT GGT ATT GAA GTT GGT GAC          585
Val Ala Leu Leu Thr Arg Lys Ile Tyr Asp Gly Ile Glu Val Gly Asp
                165                 170                 175

AGG CCT CGA GTT ATT ATC AAA GGA TAT TTC CAA GGA AAT GCT CTA ACA          633
Arg Pro Arg Val Ile Ile Lys Gly Tyr Phe Gln Gly Asn Ala Leu Thr
            180                 185                 190

GAT AGA TCC ATC GAC TTC AAT GGT AGA GTC AAA TAT GCT AAT CAT ATG          681
Asp Arg Ser Ile Asp Phe Asn Gly Arg Val Lys Tyr Ala Asn His Met
        195                 200                 205

GGA CTT ATT TCA GAT AAG ATC TAT CAG TCT GCT AAA GCA AAT TGC AAC          729
Gly Leu Ile Ser Asp Lys Ile Tyr Gln Ser Ala Lys Ala Asn Cys Asn
210                 215                 220                 225

GGG AAT TAC ATT GAC GTT GAT CCA AAT AAC ATA TTA TGC CTA AAT GAT          777
Gly Asn Tyr Ile Asp Val Asp Pro Asn Asn Ile Leu Cys Leu Asn Asp
                230                 235                 240

CTT CAG AAA GTA ACA AGG TGT CTC AAG AAC ATA CGA CGG GCG CAA ATT          825
Leu Gln Lys Val Thr Arg Cys Leu Lys Asn Ile Arg Arg Ala Gln Ile
                245                 250                 255

TTA GAG CCT TAC TGT GAC CTT CCA TAT TTA ATG GGT ATT CTC CAA GAA          873
Leu Glu Pro Tyr Cys Asp Leu Pro Tyr Leu Met Gly Ile Leu Gln Glu
            260                 265                 270

ACT CCT ACA AAT GGC CAG TCA GTA TTT CCA ATT GCA GGA CCA TGG TGT          921
Thr Pro Thr Asn Gly Gln Ser Val Phe Pro Ile Ala Gly Pro Trp Cys
        275                 280                 285

CGA GAA AAG AAT TAC ATA TAC TCG TAT GTT TGG GCA AAT GAT AAA GCT          969
Arg Glu Lys Asn Tyr Ile Tyr Ser Tyr Val Trp Ala Asn Asp Lys Ala
290                 295                 300                 305

GTC CAG AAA GCA CTA AGC GTT CGT GAG GGA ACA ACA TTG GAG TGG GTG         1017
Val Gln Lys Ala Leu Ser Val Arg Glu Gly Thr Thr Leu Glu Trp Val
                310                 315                 320

AGA TGC AAT GAA AGC ATG CAT TAT AGA GGT AAG GAG AGA ACC GAG TCA         1065
Arg Cys Asn Glu Ser Met His Tyr Arg Gly Lys Glu Arg Thr Glu Ser
                325                 330                 335

TAT GTG TAT GAT GTC CCA AGT GTC ATT GAT GAT CAT CAA CAT CTC ACC         1113
Tyr Val Tyr Asp Val Pro Ser Val Ile Asp Asp His Gln His Leu Thr
            340                 345                 350

AGC AAA TCC TGT CGA GCA CTA ATT TAC AGT GGT GAC CAT GAC ATG GTT         1161
Ser Lys Ser Cys Arg Ala Leu Ile Tyr Ser Gly Asp His Asp Met Val
355                 360                 365

GTT CCT CAT TTG AGC ACG GAG GAA TGG ATA GAG ACT TTG AAA CTT CCA         1209
Val Pro His Leu Ser Thr Glu Glu Trp Ile Glu Thr Leu Lys Leu Pro
370                 375                 380                 385

ATT GCA GAT GAT TGG GAG CCT TGG TTT GTT GAC GAT CAA GTA GCA GGA         1257
Ile Ala Asp Asp Trp Glu Pro Trp Phe Val Asp Asp Gln Val Ala Gly
                390                 395                 400

TAC AAA GTG AAG TAT TTA CAA AAT GAT TAT GAA ATG ACA TAT GCA ACT         1305
Tyr Lys Val Lys Tyr Leu Gln Asn Asp Tyr Glu Met Thr Tyr Ala Thr
            405                 410                 415

GTT AAG GGT GCG GGG CAT ACT GCT CCT GAA TAC AAG CCA GAA CAA TGC         1353
Val Lys Gly Ala Gly His Thr Ala Pro Glu Tyr Lys Pro Glu Gln Cys
        420                 425                 430
```

```
CTG CCC ATG GTT GAT AGG TGG TTT TCC GGT GAC CCT CTT TGATTTCACC     1402
Leu Pro Met Val Asp Arg Trp Phe Ser Gly Asp Pro Leu
    435                 440                 445

CTTGCAAGAC ATTAATGTAC TCATTTGTTT CTCTGGATTG ACATAAGCTT GCTTCTTTGA   1462

GCAACATCAC ATTAAGCTTG TCTGTCATGT AATCTTGACA TGTAAAATCA CACATTAAAA   1522

AGTATATATC ATTCGAGGTT GACGTTAAAA AAAAAAAAAA AAAAAAAAAA AAAAAAAAAA   1582

AAAAAAAAAA AAAAAAAAAA AA                                           1604
```

(2) INFORMATION FOR SEQ ID NO:10:

(i) SEQUENCE CHARACTERISTICS:
        (A) LENGTH: 446 amino acids
        (B) TYPE: amino acid
        (D) TOPOLOGY: linear (ii) MOLECULE TYPE: protein (xi) SEQUENCE DESCRIPTION: SEQ ID NO:10:

```
Glu His Phe Ile Val Glu Thr Leu Pro Gly Phe His Gly Lys Leu Pro
 1               5                  10                  15

Phe Thr Leu Glu Thr Gly Tyr Ile Ser Val Gly Glu Glu Lys Val
                20                  25                  30

Gln Leu Phe Tyr Phe Phe Val Gln Ser Glu Arg Asp Pro Arg Asn Asp
            35                  40                  45

Pro Leu Met Ile Trp Leu Thr Gly Gly Pro Gly Cys Ser Gly Leu Ser
    50                  55                  60

Ser Leu Val Tyr Glu Ile Gly Pro Leu Thr Phe Asp Tyr Ala Asn Ser
65                  70                  75                  80

Ser Gly Asn Phe Pro Lys Leu Glu Leu Asn Ser Tyr Ser Trp Thr Lys
                85                  90                  95

Val Ala Asn Ile Ile Phe Ile Asp Gln Pro Ala Gly Thr Gly Tyr Ser
                100                 105                 110

Tyr Ala Asn Thr Ser Glu Ala Tyr Asn Cys Asn Asp Thr Leu Ser Val
            115                 120                 125

Thr Leu Thr Tyr Asp Phe Leu Arg Lys Trp Leu Met Asp His Pro Glu
    130                 135                 140

Tyr Leu Asn Asn Pro Leu Tyr Val Gly Gly Asp Ser Tyr Ser Gly Ile
145                 150                 155                 160

Phe Val Ala Leu Leu Thr Arg Lys Ile Tyr Asp Gly Ile Glu Val Gly
                165                 170                 175

Asp Arg Pro Arg Val Ile Ile Lys Gly Tyr Phe Gln Gly Asn Ala Leu
            180                 185                 190

Thr Asp Arg Ser Ile Asp Phe Asn Gly Arg Val Lys Tyr Ala Asn His
    195                 200                 205

Met Gly Leu Ile Ser Asp Lys Ile Tyr Gln Ser Ala Lys Ala Asn Cys
    210                 215                 220

Asn Gly Asn Tyr Ile Asp Val Asp Pro Asn Asn Ile Leu Cys Leu Asn
225                 230                 235                 240

Asp Leu Gln Lys Val Thr Arg Cys Leu Lys Asn Ile Arg Arg Ala Gln
                245                 250                 255

Ile Leu Glu Pro Tyr Cys Asp Leu Pro Tyr Leu Met Gly Ile Leu Gln
                260                 265                 270

Glu Thr Pro Thr Asn Gly Gln Ser Val Phe Pro Ile Ala Gly Pro Trp
            275                 280                 285

Cys Arg Glu Lys Asn Tyr Ile Tyr Ser Tyr Val Trp Ala Asn Asp Lys
```

```
            290                 295                 300
Ala Val Gln Lys Ala Leu Ser Val Arg Glu Gly Thr Thr Leu Glu Trp
305                 310                 315                 320

Val Arg Cys Asn Glu Ser Met His Tyr Arg Gly Lys Glu Arg Thr Glu
                325                 330                 335

Ser Tyr Val Tyr Asp Val Pro Ser Val Ile Asp Asp His Gln His Leu
            340                 345                 350

Thr Ser Lys Ser Cys Arg Ala Leu Ile Tyr Ser Gly Asp His Asp Met
            355                 360                 365

Val Val Pro His Leu Ser Thr Glu Glu Trp Ile Glu Thr Leu Lys Leu
370                 375                 380

Pro Ile Ala Asp Asp Trp Glu Pro Trp Phe Val Asp Asp Gln Val Ala
385                 390                 395                 400

Gly Tyr Lys Val Lys Tyr Leu Gln Asn Asp Tyr Glu Met Thr Tyr Ala
                405                 410                 415

Thr Val Lys Gly Ala Gly His Thr Ala Pro Glu Tyr Lys Pro Glu Gln
                420                 425                 430

Cys Leu Pro Met Val Asp Arg Trp Phe Ser Gly Asp Pro Leu
                435                 440                 445
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GARCAYTTYA TYGTKGARAC                                  20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 3
        (D) OTHER INFORMATION: /note= "N is inosine"

(xi) SEQUENCE DESCRIPTION: SEQ ID NO:12:

ARNCCCATRT GRTTWGCRTA                                  20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATCTGTTAGA GCATTGCCTT                                  20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCCTGTCACC AACTTCAATA                                              20

(2) INFORMATION FOR SEQ ID NO:15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 36
        (D) OTHER INFORMATION: /note= "N is inosine"

(ix) FEATURE:
        (A) NAME/KEY: misc_feature
        (B) LOCATION: 37
        (D) OTHER INFORMATION: /note= "N is inosine"

(ix) FEATURE:
        (A) NAME/KEY: misc_feature
        (B) LOCATION: 41
        (D) OTHER INFORMATION: /note= "N is inosine"

(ix) FEATURE:
        (A) NAME/KEY: misc_feature
        (B) LOCATION: 42
        (D) OTHER INFORMATION: /note= "N is inosine"

(ix) FEATURE:
        (A) NAME/KEY: misc_feature
        (B) LOCATION: 46
        (D) OTHER INFORMATION: /note= "N is inosine"

(ix) FEATURE:
        (A) NAME/KEY: misc_feature
        (B) LOCATION: 47
        (D) OTHER INFORMATION: /note= "N is inosine"

(xi) SEQUENCE DESCRIPTION: SEQ ID NO:15:

CUACUACUAC UAGGCCACGC GTCGACTAGT ACGGGNNGGG NNGGGNNG            48

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GTTGGAGAAG AGGAAAAAGT                                              20

(2) INFORMATION FOR SEQ ID NO:17:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TACAATCTGA GAGAGACCCA                                               20

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AAGGATCCAA TGGCGCGGGT CACACTGTT                                     29

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AGAATTCTTA ACGTCAACCT CGAATGA                                       27
```